United States Patent
Chen et al.

(10) Patent No.: US 8,704,007 B2
(45) Date of Patent: *Apr. 22, 2014

(54) HYDROCONVERSION OF RENEWABLE FEEDSTOCKS

(75) Inventors: Cong-Yan Chen, Kensington, CA (US); Alexander E. Kuperman, Orinda, CA (US); William J. Cannella, Orinda, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 314 days.

This patent is subject to a terminal disclaimer.

(21) Appl. No.: 13/315,611

(22) Filed: Dec. 9, 2011

(65) Prior Publication Data

US 2013/0150631 A1    Jun. 13, 2013

(51) Int. Cl.
*C07C 27/04* (2006.01)

(52) U.S. Cl.
USPC .......................... 568/864; 554/169

(58) Field of Classification Search
USPC .......................... 568/864; 554/169
See application file for complete search history.

(56) References Cited

U.S. PATENT DOCUMENTS

| | | | |
|---|---|---|---|
| 2,094,127 A | 9/1937 | Lazier | |
| 2,109,844 A | 3/1938 | Lazier | |
| 2,241,417 A | 5/1941 | Normann | |
| 4,942,266 A | 7/1990 | Fleckenstein et al. | |
| 4,982,020 A | 1/1991 | Carduck et al. | |
| 5,233,099 A | 8/1993 | Tabata et al. | |
| 5,364,986 A | 11/1994 | Demmering et al. | |
| 5,366,658 A | 11/1994 | Hoppe et al. | |
| 5,475,160 A | 12/1995 | Singleton et al. | |
| 6,156,695 A | 12/2000 | Soled et al. | |
| 6,162,350 A | 12/2000 | Soled et al. | |
| 7,544,850 B2 | 6/2009 | Goze et al. | |
| 7,579,508 B2 | 8/2009 | Sakamoto et al. | |
| 7,667,059 B2 | 2/2010 | Sakamoto et al. | |
| 7,807,599 B2 | 10/2010 | Maesen et al. | |
| 7,888,542 B2 | 2/2011 | Koivusalmi et al. | |
| 8,097,740 B2 | 1/2012 | Miller | |
| 8,324,438 B2 | 12/2012 | Brandvold et al. | |
| 2009/0107889 A1 | 4/2009 | Maesen et al. | |
| 2009/0166256 A1 | 7/2009 | Lewis et al. | |
| 2009/0255171 A1 | 10/2009 | Dumesic et al. | |
| 2011/0047862 A1 | 3/2011 | Mayeur et al. | |
| 2011/0094149 A1 | 4/2011 | Weiss et al. | |
| 2011/0155636 A1 | 6/2011 | Hanks et al. | |
| 2011/0163009 A1 | 7/2011 | Novak et al. | |
| 2012/0000824 A1 | 1/2012 | Dougherty et al. | |
| 2012/0016167 A1 | 1/2012 | Hanks | |
| 2012/0053099 A1 | 3/2012 | Zhou et al. | |
| 2012/0216450 A1 | 8/2012 | Dupassieux et al. | |
| 2012/0283151 A1 | 11/2012 | Espagne et al. | |

OTHER PUBLICATIONS

U.R. Kreutzer "Manufacture of Fatty Alcohols Based on Natural Fats and Oils" J. Am. Oil Chem. Soc. 1984, 61, 343-348.
U.S. Appl. No. 13/315,575, filed Dec. 9, 2011, Chen.
U.S. Appl. No. 13/315,650, filed Dec. 9, 2011, Chen.
U.S. Appl. No. 13/315,683, filed Dec. 9, 2011, Chen.
U.S. Appl. No. 13/315,729, filed Dec. 9, 2011, Chen.
U.S. Appl. No. 13/315,774, filed Dec. 9, 2011, Chen.
U.S. Appl. No. 13/708,811, filed Dec. 7, 2012, Chen.

*Primary Examiner* — Elvis O Price

(57) ABSTRACT

A hydrocarbon conversion process comprises contacting a renewable feedstock under hydroprocessing conditions with a bulk catalyst to form oleochemicals such as fatty alcohols, esters, and normal paraffins. Advantageously, the reaction conditions can be selected to directly convert the renewable feedstock to the desired product(s).

15 Claims, No Drawings

HYDROCONVERSION OF RENEWABLE FEEDSTOCKS

TECHNICAL FIELD

The application relates generally to a process for converting renewable feedstocks to oleochemicals such as fatty alcohols, esters, and normal paraffins by contacting the feedstock with a bulk multi-metallic catalyst under hydroprocessing conditions.

BACKGROUND

Fossil fuels are a finite, non-renewable resource formed from decayed plants and animals that have been converted to crude oil, coal, natural gas, or heavy oils by exposure to heat and pressure in the earth's crust over hundreds of millions of years. However, as the world's petroleum resources are depleting coupled with its ever-increasing prices, many industries worldwide have been looking into renewable/sustainable raw materials to replace petroleum-based materials in their manufacturing processes.

Industrial oleochemicals are useful in the production of surfactants, lubricants, fuels, plastics, and the like. Oleochemicals include, but are not limited to, fatty alcohols, esters and paraffins. Providing efficient processes for directly converting renewable materials into such products would be highly desirable.

SUMMARY

In one aspect, there is provided a hydrocarbon conversion process comprising contacting a renewable feedstock, under hydroprocessing conditions, with a bulk catalyst to form an effluent and recovering a fatty alcohol fraction from the effluent, wherein the hydroprocessing conditions include a temperature of from 383° F. to 464° F. (195° C. to 240° C.) and a total reaction pressure of from 800 to 2000 psig (5.5 to 13.8 MPa gauge).

In another aspect, there is provided a hydrocarbon conversion process comprising contacting a renewable feedstock, under hydroprocessing conditions, with a bulk catalyst to form an effluent and recovering an aliphatic monoester fraction from the effluent, wherein the hydroprocessing conditions include a temperature of from 383° F. to 464° F. (195° C. to 240° C.) and a total reaction pressure of from 800 to 2000 psig (5.5 to 13.8 MPa gauge).

In yet another aspect, there is provided hydrocarbon conversion process comprising contacting a renewable feedstock, under hydroprocessing conditions, with a bulk catalyst to form an effluent and recovering a hydrocarbon fraction comprising normal paraffins from the effluent, wherein the hydroprocessing conditions include a temperature of from 491° F. to 662° F. (255° C. to 350° C.) and a total reaction pressure of from 800 to 2000 psig (5.5 to 13.8 MPa gauge).

DETAILED DESCRIPTION

The following terms will be used throughout the specification and will have the following meanings unless otherwise indicated.

The term "renewable feedstock" is meant to include feedstocks other than those obtained from crude oil.

The term "oleochemical" refers to a chemical that is biologically-derived, i.e., from a renewable resource of biological origin. Such a term is generally accepted as being exclusive of fossil fuels.

A "middle distillate" is a hydrocarbon product having a boiling range of from 250° F. to 1100° F. (121° C. to 593° C.). The term "middle distillate" includes the diesel, heating oil, jet fuel, and kerosene boiling range fractions. It may also include a portion of naphtha or light oil. A "jet fuel" is a hydrocarbon product having a boiling range in the jet fuel boiling range. The term "jet fuel boiling range" refers to hydrocarbons having a boiling range of from 280° F. to 572° F. (138° C. to 300° C.). The term "diesel fuel boiling range" refers to hydrocarbons having a boiling range of from 250° F. to 1000° F. (121° C. to 538° C.). The "boiling range" is the 10 vol. % boiling point to the final boiling point (99.5 vol. %), inclusive of the end points, as measured by ASTM D2887-08 ("Standard Test Method for Boiling Range Distribution of Petroleum Fractions by Gas Chromatography").

The term "triglyceride," refers to class of molecules having the general formula (1):

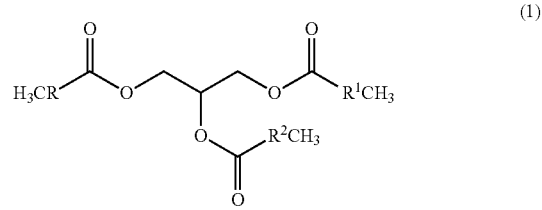

(1)

wherein R, $R^1$ and $R^2$ are independently aliphatic residues having from 6 to 22 carbon atoms (e.g., from 8 to 20 carbon atoms, or from 10 to 16 carbon atoms). The term "aliphatic" means a straight (i.e., un-branched) or branched, substituted or un-substituted hydrocarbon chain that is completely saturated or that contains one or more units of unsaturation.

The term "fatty alcohol" refers to primary aliphatic alcohols generally having from 8 to 24 carbon atoms, usually from 8 to 18 carbon atoms.

The term "aliphatic monoester" refers to compounds having the general formula (2):

(2)

wherein $R^3$ and $R^4$ are independently alkyl moieties, $R^4$ is an alkyl moiety having at least 8 carbon atoms, and the total carbon number of the aliphatic monoester is at least 14. In some embodiments, the aliphatic ester has from 16 to 40 carbon atoms (e.g., from 18 to 36, or from 20 to 34 carbon atoms). Such esters can be useful as lubricants.

The term "paraffin" refers to any saturated hydrocarbon compound, i.e., an alkane having the formula $C_nH_{(2n+2)}$ where n is a positive non-zero integer.

The term "normal paraffin" refers to a saturated straight chain hydrocarbon.

The term "isoparaffin" refers to a saturated branched chain hydrocarbon.

The term "hydroconversion" can be used interchangeably with the term "hydroprocessing" and refers to any process that is carried out in the presence of hydrogen and a catalyst. Such processes include, but are not limited to, methanation, water gas shift reactions, hydrogenation, hydrotreating, hydrodesulfurization, hydrodenitrogenation, hydrodeoxygenation, hydrodemetallation, hydrodeoxygenation, hydrodearomatization, hydroisomerization, hydrodewaxing and hydrocracking including selective hydrocracking The term "isomerizing" refers to catalytic process in which a normal paraffin is converted at least partially into an isoparaffin. Such isomerization generally proceeds by way of a catalytic route.

The term "bulk catalyst" can be used interchangeably with "unsupported catalyst," or "self-supported catalyst," meaning that the catalyst composition is NOT of the conventional catalyst form which has a preformed, shaped catalyst support which is then loaded with metal compounds via impregnation or deposition catalyst. In one embodiment, the bulk catalyst is formed through precipitation. In another embodiment, the bulk catalyst has a binder incorporated into the catalyst composition. In yet another embodiment, the bulk catalyst is formed from metal compounds and without any binder.

The term "catalyst precursor" refers to a compound containing at least a promoter metal selected from Group IIA, Group IIB, Group IVA, Group VIII metals and combinations thereof (i.e., one or more Group IIA metals, one or more Group IIB metals, one or more Group IVA metals, one or more Group VIII metals, and combinations thereof); at least a Group VIB metal; an oxide or a hydroxide; and, optionally, one or more organic oxygen-containing ligands, and which compound can be catalytically active after sulfidation as a hydroprocessing catalyst.

The term "Group IIA" or "Group IIA metal" refers to beryllium (Be), magnesium (Mg), calcium (Ca), strontium (Sr), barium (Ba), radium (Ra), and combinations thereof in their elemental, compound, or ionic form.

The term "Group IIB" or "Group IIB metal" refers to zinc (Zn), cadmium (Cd), mercury (Hg), and combinations thereof in their elemental, compound, or ionic form.

The term "Group IVA" or "Group IVA metal" refers to germanium (Ge), tin (Sn) or lead (Pb), and combinations thereof in their elemental, compound, or ionic form.

The term "Group VIB" or "Group VIB metal" refers to chromium (Cr), molybdenum (Mo), tungsten (W), and combinations thereof in their elemental, compound, or ionic form.

The term "Group VIII" or "Group VIII metal" refers to iron (Fe), cobalt (Co), nickel (Ni), ruthenium (Ru), rhenium (Re), palladium (Pd), osmium (Os), iridium (Ir), platinum (Pt), and combinations thereof in their elemental, compound, or ionic form.

When used herein, the Periodic Table of the Elements refers to the version published by the CRC Press in the CRC *Handbook of Chemistry and Physics,* 88th Edition (2007-2008). The names for families of the elements in the Periodic Table are given here in the Chemical Abstracts Service (CAS) notation.

The term "conversion" refers to the amount of triglycerides in the feed that is converted to compounds other than triglycerides. Conversion is expressed as a weight percentage based on triglycerides in the feed. "Selectivity" is expressed as a weight percent based on converted triglycerides. It should be understood that each compound converted from triglycerides has an independent selectivity and that selectivity is independent from conversion.

Feed

The renewable feedstocks that can be used include any of those which comprise triglycerides. The feedstock generally originates from a biomass source selected from the group consisting of crops, vegetables, microalgae, animal fats, and combinations thereof. The feedstock generally comprises at least 25 wt. % triglycerides (e.g., at least 50 wt. %, 75 wt. %, 90 wt. %, or 95 wt. % triglycerides). Those of skill in the art will recognize that generally any biological source of lipids can serve as the biomass from which the feedstock can be obtained. It will be further appreciated that some such sources are more economical and more amenable to regional cultivation, and also that those sources from which food is not derived can be additionally attractive (so as not to be seen as competing with food). Exemplary feedstocks include, but are not limited to canola oil, coconut oil, palm oil, palm kernel oil, peanut oil, rapeseed oil, soybean oil, and the like.

Hydroprocessing Catalyst

The bulk catalyst is derived from a catalyst precursor. The catalyst precursor can be a hydroxide or oxide material, prepared from at least a promoter metal precursor feed and at least a Group VIB metal precursor feed. "Promoter metal" can be used interchangeably with $M^P$, referring to a material that enhances the activity of a catalyst (as compared to a catalyst without the promoter metal, e.g., a catalyst with just a Group VIB metal). The bulk or unsupported catalyst precursor made can be converted into a hydroconversion bulk catalyst (becoming catalytically active) upon sulfidation.

Further details regarding the description of the catalyst precursor and the bulk catalyst formed thereof are described in a number of patents and patent applications, including U.S. Pat. Nos. 6,156,695; 6,162,350; 6,274,530; 6,299,760; 6,566, 296; 6,620,313; 6,635,599; 6,652,738; 6,758,963; 6,783,663; 6,860,987; 7,179,366; 7,229,548; 7,232,515; 7,288,182; 7,544,285; 7,615,196; 7,803,735; 7,807,599; 7,816,298; 7,838,696; 7,910,761; 7,931,799; 7,964,524; 7,964,525; 7,964,526; 8,058,203; and U.S. Pat. Application Publication Nos. 2007/0090024, 2009/0107886, 2009/0107883, 2009/0107889 and 2009/0111683.

In one embodiment, the catalyst precursor is a bulk multi-metallic oxide, comprising of at least one Group VIII non-noble material and at least two Group VIB metals. In one embodiment, the ratio of Group VIB metal to Group VIII non-noble metal in the precursor ranges from about 10:1 to about 1:10. In another embodiment, the oxide catalyst precursor is represented by the formula (3):

$$(X)_b(Mo)_c(W)_dO_f \qquad (3)$$

wherein X is Ni or Co, the molar ratio of b: (c+d) is 0.5:1 to 3:1 (e.g., 0.75:1 to 1.5:1, or 0.75:1 to 1.25:1), the molar ratio of c: d is >0.01:1 (e.g., greater than 0.1:1, 1:10 to 10:1, or 1:3 to 3:1), and f=[2b+6 (c+d)]/2. In yet another embodiment, the oxide catalyst precursor further comprises one or more ligating agents L. The term "ligand" may be used interchangeably with "ligating agent," "chelating agent" or "complexing agent" or chelator, or chelant), referring to an additive that combines with metal ions, e.g., Group VIB and/or promoter metals, forming a larger complex, e.g., a catalyst precursor.

In another embodiment, the catalyst precursor is in the form of a hydroxide compound, comprising of at least one Group VIII non-noble material and at least two Group VIB metals. In one embodiment, the hydroxide catalyst precursor is represented by the formula (4):

$$A_v[(M^P)(OH)_x(L)^n{}_y]_z(M^{VIB}O_4) \qquad (4)$$

wherein A is one or more monovalent cationic species; $M^P$ is at least a promoter metal with an oxidation state (P) of either +2 or +4 depending on the promoter metal(s) being employed; L is one or more oxygen-containing ligands, and L has a neutral or negative charge n≤0; $M^{VIB}$ is at least a Group VIB metal having an oxidation state of +6; $M^P$:$M^{VIB}$ has an atomic ratio between 100:1 and 1:100; v−2+P*z−x*z+ n*y*z=0; and 0 <v≤2; 0<x≤P; 0<y≤−P/n; 0<z. The catalyst precursor represented by formula (4) is charge-neutral. The term "charge-neutral" refers to the fact that the catalyst precursor carries no net positive or negative charge.

In one embodiment, A is selected from the group consisting of an alkali metal cation, an ammonium cation, an organic ammonium cation and a phosphonium cation.

In one embodiment, $M^P$ has an oxidation state of either +2 or +4. $M^P$ is at least one of a Group IIA metal, Group IIB metal, Group IVA metal, Group VIII metal and combinations thereof. In one embodiment, $M^P$ is at least a Group VIII metal with $M^P$ having an oxidation state P of +2. In another embodiment, $M^P$ is selected from Group IIB metals, Group IVA metals and combinations thereof. In one embodiment, $M^P$ is selected from the group of Group IIB and Group VIA metals such as zinc, cadmium, mercury, germanium, tin or lead, and combinations thereof, in their elemental, compound, or ionic form. In another embodiment, $M^P$ is a Group IIA metal compound, selected from the group of magnesium, calcium, strontium and barium compounds. $M^P$ can be in solution or in partly in the solid state, e.g., a water-insoluble compound such as a carbonate, hydroxide, fumarate, phosphate, phosphite, sulfide, molybdate, tungstate, oxide, or mixtures thereof.

In one embodiment, the optional ligating agent L has a neutral or negative charge n ≤0. Examples of oxygen-containing ligating agents L include but are not limited to carboxylates, carboxylic acids, aldehydes, ketones, the enolate forms of aldehydes, the enolate forms of ketones, and hemiacetals; organic acid addition salts such as formic acid, acetic acid, propionic acid, maleic acid, malic acid, cluconic acid, fumaric acid, succinic acid, tartaric acid, citric acid, oxalic acid, glyoxylic acid, aspartic acid, alkane sulfonic acids such as methanesulfonic acid and ethanesulfonic acid, aryl sulfonic acids such as benzenesulfonic acid and p-toluenesulfonic acid and arylcarboxylic acids; carboxylate containing compounds such as maleate, formate, acetate, propionate, butyrate, pentanoate, hexanoate, dicarboxylate, and combinations thereof.

In one embodiment, $M^{VIB}$ is at least a Group VIB metal having an oxidation state of +6. In another embodiment, $M^{VIB}$ is a mixture of at least two Group VIB metals, e.g., molybdenum and tungsten. $M^{VIB}$ can be in solution or in partly in the solid state. In one embodiment, $M^P:M^{VIB}$ has a mole ratio of 10:1 to 1:10.

Embodiments of the process for making the unsupported or bulk catalyst precursor are as described in the references indicated above, and incorporated herein by reference. In one embodiment, the first step is a mixing step wherein at least one Group IVB metal precursor feed and at least one promoter metal precursor feed are combined together in a precipitation step (also called co-gelation or co-precipitation), wherein a catalyst precursor is formed as a gel. The precipitation (or "co-gelation") is carried out at a temperature and pH under which the promoter metal compound and the Group VIB metal compound precipitate (e.g., forming a gel). In one embodiment, the temperature is from 25° C. to 350° C. and the pressure is from 0 to 3000 psig (0 to 20.7 MPa gauge). The pH of the reaction mixture can be changed to increase or decrease the rate of precipitation (co-gelation), depending on the desired characteristics of the catalyst precursor product. In one embodiment, the mixture is left at its natural pH during the reaction step(s). In another embodiment, the pH is maintained in the range from 0 to 12.

Hydroprocessing Conditions

The hydroprocessing conditions can be selected so that an overall conversion rate of triglycerides in the feedstock is at least 20 wt. %, (e.g., at least 50 wt. %, 60 wt. %, 70 wt. %, 80 wt. %, 90 wt. %, or 95 wt. %). Suitable hydroprocessing conditions can include a temperature of from 383° F. to 662° F. (195° C. to 350° C.), e.g., from 383° F. to 464° F. (195° C. to 240° C.), 491° F. to 662° F. (255° C. to 350° C.), or from 491° F. to 563° F. (255° C. to 295° C.); a total reaction pressure of from 500 to 2000 psig (3.4 to 13.8 MPa gauge), e.g., from 800 to 2000 psig (5.5 to 13.8 MPa gauge), or from 1600 to 2000 psig (11.0 to 13.8 MPa gauge); a liquid hourly space velocity (LHSV) of from 0.1 to 5 $h^-$, e.g., from 0.5 to 2 $h^{-1}$; and a hydrogen feed rate of from 0.1 to 20 MSCF/bbl (thousand standard cubic feet per barrel), e.g., from 1 to 10 MSCF/bbl. Note that a feed rate of 10 MSCF/bbl is equivalent to 1781 L $H_2$/L feed.

The hydroprocessing process can be single-staged or multiple-staged. In one embodiment, the process utilizes a single-stage system. Catalysts prepared from the catalyst precursor can be applied in any reactor type. In one embodiment, the catalyst is applied to a fixed bed reactor.

If desired, unreacted triglycerides can be recycled to the reaction system for further processing to maximize production of the desired product(s).

Products

The effluent from the hydroprocessing zone will comprise a liquid portion and a gaseous portion. After hydroprocessing, the effluent can be passed to one or more separators/fractionators for the removal of gas phase products (e.g., CO, $CO_2$, methane and propane) and separation of one or more fully and/or partially deoxygenated product fractions (e.g., n-paraffins, fatty alcohols and/or aliphatic monoesters) from the liquid portion. Different feedstocks will result in different carbon distributions of liquid products.

In one embodiment, the liquid product is a product selected from the group of a fatty alcohol, an aliphatic monoester, and normal paraffins. In another embodiment, the product is a fatty alcohol, an aliphatic monoester, or a combination thereof. The hydroprocessing conditions can be selected from any parameter that influences the subsequent level of the desired product(s) in the effluent from the reactor. In one aspect, the hydroprocessing parameter is one that obtains a yield of a product in the reactant mixture, increases the yield of a product, optimizes the selectivity of products in the reactor, or is effective for a conversion of triglycerides in the reactor. In one embodiment, the hydroprocessing parameter is selected from the group consisting of a reactor temperature, a reactor pressure and combinations thereof.

In some embodiments, the effluent comprises a fatty alcohol fraction. In some embodiments, the effluent comprises at least 5 wt. % of a fatty alcohol (e.g., at least 10 wt. % of a fatty alcohol). In some embodiments, the effluent has a selectivity to a fatty alcohol of at least 10% (e.g., at least 15%, 20%, or 25%).

In some embodiments, the effluent comprises an aliphatic monoester fraction. In some embodiments, the effluent comprises at least 4 wt. % of an aliphatic monoester (e.g., at least 7 wt. %, 10 wt. % or 13 wt. %). In some embodiments, the effluent has a selectivity to an aliphatic monoester of at least 10% (e.g., at least 12%, 15%, or 18%).

In some embodiments, the effluent comprises a normal paraffin fraction. In some embodiments, the effluent comprises at least 75 wt. % of normal paraffins (e.g., at least 80 wt. % normal paraffins). In some embodiments, the normal paraffins have from 8 to 24 carbon atoms (e.g., from 12 to 18 carbon atoms).

Note that the normal paraffins can be utilized as a middle distillate fuel. However, subsequent isomerization of the normal paraffins to isoparaffins can provide a broader range of products, thereby making the process more universal and flexible.

Catalytic Isomerization

In some embodiments, such above-described processes can further comprise a step of catalytically isomerizing at least some of the normal paraffins to yield an isomerized product comprising isoparaffins. In some embodiments, the step of catalytically isomerizing results in superior fuel properties (e.g., cloud point, pour point etc.) relative to those of the non-isomerized paraffinic product.

In some embodiments, the step of isomerizing is carried out using an isomerization catalyst. Suitable such isomerization catalysts can include, but are not limited to, Pt and/or Pd on a support. Suitable supports include, but are not limited to, zeolites CIT-1, IM-5, SSZ-20,SSZ-23, SSZ-24, SSZ-25, SSZ-26, SSZ-31, SSZ-32, SSZ-32, SSZ-33, SSZ-35, SSZ-36, SSZ-37, SSZ-41, SSZ-42, SSZ-43, SSZ-44, SSZ-46, SSZ-47, SSZ-48, SSZ-51, SSZ-56, SSZ-57, SSZ-58, SSZ-59, SSZ-60, SSZ-61, SSZ-63, SSZ-64, SSZ-65, SSZ-67, SSZ-68, SSZ-69, SSZ-70, SSZ-71, SSZ-74, SSZ-75, SSZ-76, SSZ-78, SSZ-81, SSZ-82, SSZ-83, SSZ-86, SUZ-4, TNU-9, ZSM-5, ZSM-12, ZSM-22, ZSM-23, ZSM-35, ZSM-48, EMT-type zeolites, FAU-type zeolites, FER-type zeolites, MEL-type zeolites, MFI-type zeolites, MTT-type zeolites, MTW-type zeolites, MWW-type zeolites, TON-type zeolites, other molecular sieves materials based upon crystalline aluminophosphates such as SM-3, SM-7, SAPO-11, SAPO-31, SAPO-41, MAPO-11 and MAPO-31. In some embodiments, the step of isomerizing involves a Pt and/or Pd catalyst supported on an acidic support material selected from the group consisting of beta or zeolite Y molecular sieves, silica, alumina, silica-alumina, and combinations thereof. For other suitable isomerization catalysts, see, e.g., U.S. Pat. Nos. 4,859,312; 5,158,665; and 5,300,210.

Isomerization conditions can include a temperature of from 200° F. to 900° F. (93° C. to 482° C.), e.g., from 300° F. to 800° F. (149° C. to 427° C.), or from 400° F. to 800° F. (204° C. to 427° C.); a total reaction pressure of from 15 to 3000 psig (0.1 to 20.7 MPa gauge), e.g., from 50 to 2500 psig (0.3 to 17.2 MPa gauge); a LHSV of from 0.1 to 10 h$^{-1}$, e.g., from 0.25 to 5 h$^{-1}$; and a hydrogen gas treat rate of from 0.1 to 30 MSCF/bbl, e.g., from 0.2 to 20 MSCF/bbl, or from 0.4 to 10 MSCF/bbl.

With regard to the catalytic isomerization step described above, in some embodiments, the methods described herein can be conducted by contacting the normal paraffins with a fixed stationary bed of catalyst, with a fixed fluidized bed, or with a transport bed. In one embodiment, a trickle-bed operation is employed, wherein such feed is allowed to trickle through a stationary fixed bed, typically in the presence of hydrogen. For an illustration of the operation of such catalysts, see, U.S. Pat. Nos. 6,204,426 and 6,723,889.

In some embodiments, the isomerized product comprises at least 10 wt. % isoparaffins (e.g., at least 30 wt. %, 50 wt. %, or 70 wt. % isoparaffins). In some embodiments, the isomerized product has an isoparaffin to normal paraffin mole ratio of at least 5:1 (e.g., at least 10:1, 15:1, or 20:1).

In some embodiments, the isomerized product has a boiling range of from 250° F. to 1100° F. (121° C. to 593° C.), e.g., from 280° F. to 572° F. (138° C. to 300° C.), or from 250° F. to 1000° F. (121° C. to 538° C.).

In some embodiments, the isomerized product is suitable (or better suited) for use as a transportation fuel. In some such embodiments, the isomerized product is mixed or admixed with existing transportation fuels in order to create new fuels or to modify the properties of existing fuels. Isomerization and blending can be used to modulate and maintain pour point and cloud point of the fuel or other product at suitable values. In some embodiments, the normal paraffins are blended with other species prior to undergoing catalytic isomerization. In some embodiments, the normal paraffins are blended with the isomerized product.

EXAMPLES

The following illustrative examples are intended to be non-limiting.

Example 1

Soybean Oil Feed

Soybean oil was purchased from Lucky Supermarket (El Cerrito, Calif.) under the Sunny Select brand. The soybean feed had an API gravity of 21.6 (0.9223 g/mL). The triglycerides of soybean oil are derived mainly from five fatty acids (see, e.g., D. Firestone, *Physical and Chemical Characteristics of Oils, Fats, and Waxes*, 2$^{nd}$ Edition, 2006, AOCS Press, 149). Table 1 discloses the representative ranges of these fatty acids in soybean oil.

TABLE 1

| Fatty acid | Carbon atoms:Double bonds | Weight Percent |
|---|---|---|
| Palmitic acid | 16:0 | 9.7 to 13.3 |
| Stearic acid | 18:0 | 3.0 to 5.4 |
| Oleic acid | 18:1 | 17.7 to 28.5 |
| Linoleic acid | 18:2 | 49.8 to 57.1 |
| α-Linoleic acid | 18:3 | 5.5 to 9.5 |

Examples 2-8

The soybean oil feed from Example 1 was tested under hydroprocessing conditions in a single reactor over a catalyst based on a Ni—Mo—W-maleate catalyst precursor (per Example 1 of U.S. Pat. No. 7,807,599) and sulfided with dimethyl disulfide gas (per Example 6 of U.S. Pat. No. 7,807, 599). The reactor conditions included a hydrogen gas rate of 8.0 MSCF/bbl and a LHSV of 1.0 h$^{-1}$. Additional hydroprocessing conditions are set forth in Tables 2 and 3.

The composition of the whole product was determined by gas chromatography (GC) and is set forth in wt. % in Table 2. All liquid paraffinic products were normal paraffins as determined by GC with negligible amounts of isoparaffins formed. Methane and propane were essentially the only other hydrocarbon products. Water, carbon monoxide (CO), and carbon dioxide ($CO_2$) were by-products from hydrodeoxygenation, hydrodecarbonylation and/or hydrodecarboxylation.

TABLE 2

Composition of the Whole Product in Weight Percent

|  | Ex. 2 | Ex. 3 | Ex. 4 | Ex. 5 | Ex. 6 | Ex. 7 | Ex. 8 |
|---|---|---|---|---|---|---|---|
| Hydroprocessing Conditions | | | | | | | |
| Temperature, ° F. | 400 | 450 | 500 | 550 | 500 | 550 | 650 |
| Reaction Pressure, psig | 1900 | 1900 | 1900 | 1900 | 1000 | 1000 | 1000 |
| Products | | | | | | | |
| Unconverted triglycerides | 75.4 | 10.9 | <0.5 | <0.5 | <0.5 | <0.5 | <0.5 |
| n-$C_{18}$ paraffin | 4.8 | 27.9 | 54.2 | 45.1 | 46.0 | 35.1 | 23.1 |
| n-$C_{17}$ paraffin | 0.7 | 12.0 | 19.2 | 26.6 | 26.9 | 36.6 | 46.9 |
| n-$C_{16}$ paraffin | 0.6 | 3.5 | 6.6 | 6.4 | 5.7 | 4.8 | 3.8 |
| n-$C_{15}$ paraffin | 0.1 | 1.4 | 2.3 | 3.5 | 3.2 | 4.9 | 6.8 |
| $C_{18}$ alcohol | 5.8 | 9.9 | — | — | — | — | — |
| $C_{16}$ alcohol | 0.6 | 1.2 | — | — | — | — | — |
| $C_{18}$ acid | 2.7 | 4.1 | — | — | — | — | — |
| $C_{16}$ acid | 0.3 | 0.4 | — | — | — | — | — |
| $C_{18}$-$C_{18}$ ester | 3.5 | 10.2 | — | — | — | — | — |
| $C_{18}$-$C_{16}$ ester | 0.9 | 2.6 | — | — | — | — | — |
| $C_{16}$-$C_{16}$ ester | 0.1 | 0.2 | — | — | — | — | — |
| Unknown heavies | 1.6 | 2.5 | — | — | — | — | — |
| Propane | 1.2 | 4.4 | 4.9 | 5.0 | 4.9 | 5.0 | 4.8 |
| Methane | 0.02 | 0.04 | 0.2 | 0.8 | 0.1 | 0.2 | 1.1 |
| $H_2O$ | 1.6 | 6.6 | 9.8 | 9.7 | 8.9 | 7.5 | 7.4 |
| CO | 0.1 | 0.7 | 0.4 | 0.4 | 2.0 | 2.1 | 1.8 |
| $CO_2$ | 0.1 | 1.5 | 2.4 | 2.5 | 2.3 | 3.8 | 4.3 |

With reference to the examples hydroprocessed at 1900 psig and temperatures of 500° F. and 550° F. (Examples 4 and 5), both the $C_{15}/C_{16}$ n-paraffin and $C_{17}/C_{18}$ n-paraffin product ratios were 0.35 at 500° F. (Example 4). At 550° F. (Example 5), the $C_{15}/C_{16}$ n-paraffin product ratio increased to 0.55 while the $C_{17}/C_{18}$ n-paraffin product ratio increased to 0.59. The increase in the $C_{15}/C_{16}$ and $C_{17}/C_{18}$ n-paraffin product ratios indicated enhanced selectivity of this catalyst for hydrodecarboxylation and/or hydrodecarbonylation (making $C_{15}$ and $C_{17}$ n-paraffins as well as CO and $CO_2$) over hydrodeoxygenation (making $C_{16}$ and $C_{18}$ n-paraffins as well as water) at higher reaction temperatures. Accordingly, a slightly higher (CO+$CO_2$)/$H_2O$ product ratio was achieved at higher temperatures, also reflecting some enhanced selectivity for hydrodecarboxylation and/or hydrodecarbonylation over hydrodeoxygenation.

With reference to the examples hydroprocessed at 1000 psig, the $C_{15}/C_{16}$ n-paraffin product ratio at 500° F. (Example 6) was 0.56 while the $C_{17}/C_{18}$ n-paraffin ratio was 0.59. At 550° F. (Example 7), the $C_{15}/C_{16}$ n-paraffin product ratio increased to 1.02 while the $C_{17}/C_{18}$ n-paraffin product ratio increased to 1.04. In addition, at 650° F. (Example 8), the $C_{15}/C_{16}$ n-paraffin product ratio increased to 1.80 while the $C_{17}/C_{18}$ n-paraffin product ratio increased to 2.03. The increase in the $C_{15}/C_{16}$ and $C_{17}/C_{18}$ n-paraffin product ratios indicated enhanced selectivity of this catalyst for hydrodecarboxylation and/or hydrodecarbonylation (making $C_{15}$ and $C_{17}$ n-paraffins as well as CO and $CO_2$) over hydrodeoxygenation (making $C_{16}$ and $C_{18}$ n-paraffins as well as water) at higher reaction temperatures. Accordingly, higher (CO+$CO_2$)/$H_2O$ product ratios were achieved at higher temperatures, also reflecting the enhanced selectivity for hydrodecarboxylation and/or hydrodecarbonylation over hydrodeoxygenation.

Furthermore, in comparing the results of Examples 4 and 5 (run at 1900 psig) to those of Example 6 and 7 (run at 1000 psig) respectively, enhanced selectivity for hydrodecarboxylation and/or hydrodecarbonylation over hydrodeoxygenation was achieved at lower reaction pressure, leading to further reduction of hydrogen consumption.

The conversion rate of triglycerides and product selectivity of the hydroprocessing runs are set forth in Table 3.

TABLE 3

Conversion of Triglycerides and Product Selectivity

|  | Ex. 2 | Ex. 3 | Ex. 4 | Ex. 5 | Ex. 6 | Ex. 7 | Ex. 8 |
|---|---|---|---|---|---|---|---|
| Hydroprocessing Conditions | | | | | | | |
| Temperature, ° F. | 400 | 450 | 500 | 550 | 500 | 550 | 650 |
| Reaction Pressure, psig | 1900 | 1900 | 1900 | 1900 | 1000 | 1000 | 1000 |
| Products | | | | | | | |
| Conversion of triglycerides, wt. % | 24.6 | 89.1 | >99.5 | >99.5 | >99.5 | >99.5 | >99.5 |
| Product Selectivity, % | | | | | | | |
| n-$C_{18}$ paraffin | 19.3 | 31.3 | 54.2 | 45.1 | 46.0 | 35.1 | 23.1 |
| n-$C_{17}$ paraffin | 3.0 | 13.4 | 19.2 | 26.6 | 26.9 | 36.6 | 46.9 |
| n-$C_{16}$ paraffin | 2.4 | 3.9 | 6.6 | 6.4 | 5.7 | 4.8 | 3.8 |

TABLE 3-continued

Conversion of Triglycerides and Product Selectivity

|  | Ex. 2 | Ex. 3 | Ex. 4 | Ex. 5 | Ex. 6 | Ex. 7 | Ex. 8 |
|---|---|---|---|---|---|---|---|
| n-$C_{15}$ paraffin | 0.3 | 1.6 | 2.3 | 3.5 | 3.2 | 4.9 | 6.8 |
| $C_{18}$ alcohol | 23.7 | 11.2 | — | — | — | — | — |
| $C_{16}$ alcohol | 2.6 | 1.3 | — | — | — | — | — |
| $C_{18}$ acid | 11.1 | 4.7 | — | — | — | — | — |
| $C_{16}$ acid | 1.2 | 0.5 | — | — | — | — | — |
| $C_{18}$-$C_{18}$ ester | 14.1 | 11.5 | — | — | — | — | — |
| $C_{18}$-$C_{16}$ ester | 3.7 | 2.9 | — | — | — | — | — |
| $C_{16}$-$C_{16}$ ester | 0.2 | 0.2 | — | — | — | — | — |
| Unknown heavies | 6.4 | 2.8 | — | — | — | — | — |
| Propane | 4.9 | 4.9 | 4.9 | 5.0 | 4.9 | 5.0 | 4.8 |
| Methane | 0.1 | 0.1 | 0.2 | 0.8 | 0.1 | 0.2 | 1.1 |
| $H_2O$ | 6.4 | 7.4 | 9.8 | 9.7 | 8.9 | 7.5 | 7.4 |
| CO | 0.4 | 0.8 | 0.4 | 0.4 | 2.0 | 2.1 | 1.8 |
| $CO_2$ | 0.2 | 1.7 | 2.4 | 2.5 | 2.3 | 3.8 | 4.3 |

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. To an extent not inconsistent herewith, all citations referred to herein are hereby incorporated by reference.

The invention claimed is:

1. A hydrocarbon conversion process, comprising:
    a) contacting a renewable feedstock, under hydroprocessing conditions, with a bulk catalyst to form an effluent; and
    b) recovering a fatty alcohol fraction from the effluent, wherein the hydroprocessing conditions include a temperature of from 383° F. to 464° F. (195° C. to 240° C.) and a total reaction pressure of from 800 to 2000 psig (5.5 to 13.8 MPa gauge).

2. The process of claim 1, having a triglyceride conversion rate of at least 20 wt. %.

3. The process of claim 1, wherein the feedstock comprises at least 50 wt. % triglycerides.

4. The process of claim 1, wherein the feedstock originates from a biomass source selected from the group consisting of crops, vegetables, microalgae, animal fats, and combinations thereof.

5. The process of claim 1, wherein the feedstock is selected from the group consisting of canola oil, coconut oil, palm oil, palm kernel oil, peanut oil, rapeseed oil, soybean oil, and combinations thereof.

6. The process of claim 1, wherein the bulk catalyst, prior to sulfidation, is represented by the formula:

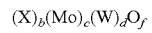
$$(X)_b(Mo)_c(W)_dO_f$$

wherein X is Ni or Co, the molar ratio of b:(c+d) is 0.5:1 to 3:1, the molar ratio of c:d is >0.01:1, and f=[2b+6(c+d)]/2.

7. The process of claim 1, wherein the bulk catalyst, prior to sulfidation, is represented by the formula:

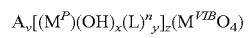
$$A_v[(M^P)(OH)_x(L)^n_y]_z(M^{VIB}O_4)$$

wherein
  a) A is selected from the group consisting of an alkali metal cation, an ammonium cation, an organic ammonium cation and a phosphonium cation;
  b) $M^P$ is at least one of a Group IIA metal, Group IIB metal, Group IVA metal, Group VIII metal and combinations thereof, P is oxidation state with $M^P$ having an oxidation state of +2 or +4 depending on the selection of $M^P$;
  c) L is at least one organic oxygen-containing ligand, and L has a neutral or negative charge n≤0;
  d) $M^{VIB}$ is at least one Group VIB metal having an oxidation state of +6;
  e) $M^P$:$M^{VIB}$ has an atomic ratio between 100:1 and 1:100;
  f) v−2 +P*z−x*z+n*y*z=0; and
  g) 0<v≤2; 0<x≤P; 0<y≤−P/n; 0<z.

8. The process of claim 5, wherein $M^P$ is Ni and $M^{VIB}$ is selected from the group consisting of Mo, W, and combinations thereof, and wherein Ni:(Mo+W) has a molar ratio of 10:1 to 1:10.

9. The process of claim 1, wherein the pressure is from 1600 to 2000 psig (11.0 to 13.8 MPa gauge).

10. The process of claim 1, wherein the effluent comprises at least 5 wt. % of a fatty alcohol.

11. The process of claim 1, wherein the effluent comprises at least 10 wt. % of a fatty alcohol.

12. The process of claim 1, having a fatty alcohol selectivity in the effluent of at least 10%.

13. The process of claim 1, having a fatty alcohol selectivity in the effluent of at least 20%.

14. The process of claim 1, wherein the fatty alcohol has from 8 and 24 carbon atoms.

15. The process of claim 1, wherein the fatty alcohol has from 8 to 18 carbon atoms.

* * * * *